United States Patent [19]

Pearson et al.

[11] Patent Number: 5,497,923
[45] Date of Patent: Mar. 12, 1996

[54] SUSPENDER SUPPORTED BELT

[76] Inventors: David P. Pearson, 861 Boxthorn Ave., Newbury Park, Calif. 91320; Conrad W. Tanner, 3140 Del Vina St., Pasadena, Calif. 91107

[21] Appl. No.: 388,727

[22] Filed: Feb. 15, 1995

Related U.S. Application Data

[63] Continuation of Ser. No. 103,526, Aug. 9, 1993, abandoned.

[51] Int. Cl.⁶ ......................................................... A45F 5/00
[52] U.S. Cl. .......................... 224/253; 224/209; 224/216; 224/226; 224/260; 224/901; 224/904; 2/300; 2/338
[58] Field of Search ........................... 224/209, 214–216, 224/224, 226, 253, 257–260, 901, 904, 255; 2/300, 310–312, 318–320, 336, 338; 128/95.1, 96.1, 100.1, 101.1, 845, 876; 602/19

[56] References Cited

U.S. PATENT DOCUMENTS

| | | | |
|---|---|---|---|
| 54,807 | 5/1866 | Woods | 224/215 X |
| 3,543,977 | 12/1970 | Lockridge | 224/901 X |
| 3,920,008 | 11/1975 | Lehman | 128/96.1 |
| 4,165,826 | 8/1979 | Chica | 224/901 X |
| 4,245,628 | 1/1981 | Eichler | 602/19 |
| 4,320,863 | 3/1982 | Lyer et al. | 224/259 |
| 4,804,025 | 2/1989 | Bear | 224/901 X |
| 4,957,231 | 9/1990 | Kalisher | 224/253 X |
| 5,064,108 | 11/1991 | Headley | 224/253 |
| 5,086,759 | 2/1992 | Boddingh | 602/19 |
| 5,240,156 | 8/1993 | Sicotte et al. | 224/224 X |
| 5,263,618 | 11/1993 | Talavera | 224/901 X |
| 5,349,706 | 9/1994 | Keer | 2/300 |
| 5,388,274 | 2/1995 | Glover et al. | 2/338 |
| 5,399,151 | 3/1995 | Smith | 602/19 |
| 5,413,262 | 5/1995 | Dewire et al. | 224/253 |

FOREIGN PATENT DOCUMENTS 8803461   5/1988   WIPO ................................. 224/904

*Primary Examiner*—J. Casimer Jacyna
*Attorney, Agent, or Firm*—Cislo & Thomas

[57] ABSTRACT

A utility belt or the like device in one embodiment capable of also acting as a back support, either suspenderless or being suspendered, to receive in secure fashion utility pouches and the like so that the utility pouches are rigidly and releasably secured and not liable to shift in relation to the belt which supports them. The extensive use of hook and loop fastener surfaces enables the device to accommodate a wide range of body shapes in a facile manner and to receive hook and loop fastener surface provided tools in releasable engagement therewith.

20 Claims, 2 Drawing Sheets

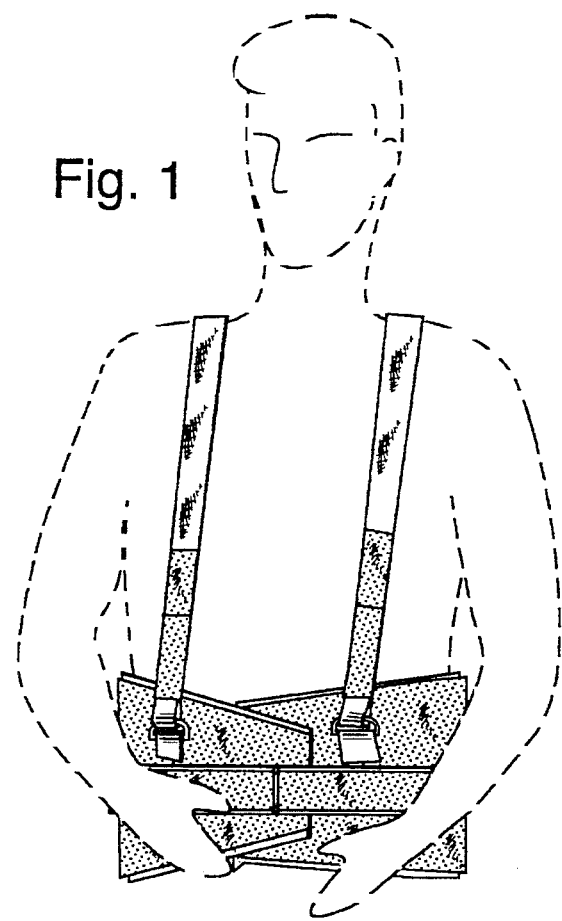
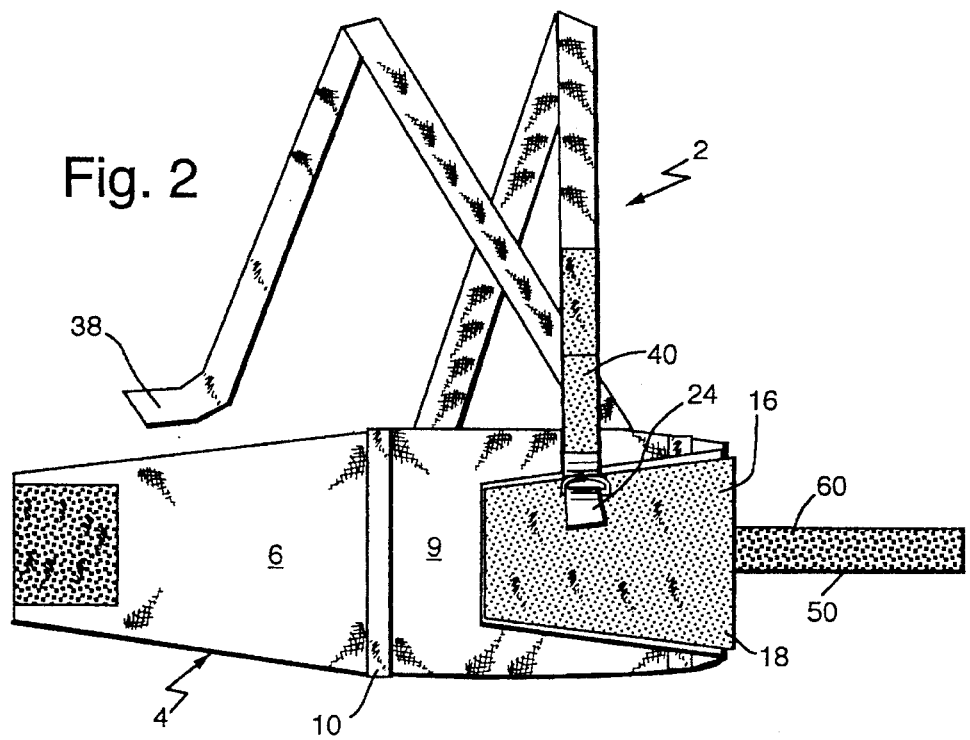

5,497,923

SUSPENDER SUPPORTED BELT

This is a continuation of application Ser. No. 08/103,526 filed on Aug. 9, 1993, now abandoned.

FIELD OF THE INVENTION

This invention pertains to a utility belt or the like which may or may not utilize suspenders and which will keep pouches supported therefrom in secure, non-slideable relationship thereto. In another embodiment and where suspenders are used, the wearer of the support may not only be able to obtain some back support while wearing the belt, but will be able to take some of the weight, from pouches or the like that are suspended from the belt encircling the back support, transferred to and carried by the shoulders. In its simplest form, the back support of the current invention has a means of receiving one or more pouches or the like that may be positioned at almost any selected useful position with respect to the waist of the user of the belt. The belt is capable of supporting an associated pouch or container for holding a variety of articles, from tools to coins, in secured relationship thereto. The belt and back support of the invention makes it easier for people who must carry relatively heavy loads to do their jobs more effectively and safely.

BACKGROUND OF THE INVENTION

Belts and back supports have been around for a considerable length of time and most recently, employers have come to recognize that it is important, from a safe workplace standpoint, to ensure that employees do not suffer on-the-job injuries for a myriad of reasons.

Literally thousands of manhours of labor are lost each year to workers incurring back injuries due to the nature of their work and the inappropriate conditioning of the workers taken in conjunction with the high demands made upon that worker's back. Various back supports have been suggested, some with and without suspenders, in order to attempt to overcome some of the difficulties normally encountered by a worker in the field.

Workers who must carry tools, for example, a carpenter, usually utilize pouches or the like having a loop at the upper portion thereof which permits placement of the pouch onto the belt for supported engagement about the waist of the carpenter. Some prior art devices have suggested the combination of such a belt with a back support in order to alleviate some of the strain and stress that a carpenter, for example, would incur on the job. Such belts and back support combinations have not been totally effective even when suspenders are utilized to help support the weight of the tools contained in the pouch inasmuch as the pouch has been allowed to be retained on the belt and back support by a loose configuration so that the pouch would move about the belt due to the carpenter's working activities.

In other instances, people who must carry substantial weights, such as, for example, coins in a slot machine gambling environment, in pockets or pouches provided on various belts have found it difficult to carry such loads in a fashion that permits ease of access and yet will not travel along the supporting belt about the waist of the wearer.

Having a supported pouch or container that is continuously moving or shifting about the waist of the worker such as a plumber, carpenter or electrician, creates several problems with respect to weight distribution and ease of access, not to mention mobility of the worker. Additionally, the conventional and ubiquitously found pouches being supported by a leather belt or the like has created difficulties in not being more porous to allow breathing or passage of the ambient atmosphere with regard to the wearer of the belt. That is, a heavy leather belt does not easily allow the passage of air or moisture therethrough, thereby making for an uncomfortable wearing situation for the wearer of the belt.

Additionally, where back support and tool pouch devices have been utilized, suspenders utilized to help defray the load from the hips and transfer to the shoulders have suffered in not being truly adjustable to the body of the user, and not being easily taken on and off by the wearer. Additionally, wearers/tradesmen depend on having easy access to tape measures, pencils and the like, as, for example, in a carpentry situation, these workmen have had to fumble to attain easy access to the tools immediately needed for the task at hand. Fumbling around in a pouch or looking for a rule and pencil has been time-consuming and counterproductive.

Currently available back support members and utility tool belt devices have not fulfilled all of the needs of various tradespeople who rely upon being able to have their tools and utensils at hand in ready fashion and further require that a back support or like member be easily put on and taken off, as well as providing for adequate support.

As exemplary of some of the prior art, a search of the U.S. Patent Office records was conducted and the following patents were uncovered by the search:

| U.S. Pat. No. | Inventor | Issue Date |
| --- | --- | --- |
| 2,910,804 | White | Nov. 03, 1959 |
| 2,976,541 | Williams | Mar. 28, 1961 |
| 3,963,157 | Truax et al | June 15, 1976 |
| 4,139,130 | Glusker et al | Feb. 13, 1979 |
| 4,166,557 | Conley | Sep. 04, 1979 |
| 4,472,839 | Johansen | Sep. 25, 1984 |
| 4,715,839 | Ford et al | Dec. 29, 1987 |
| 4,771,478 | Bisagno et al | Sep. 20, 1988 |
| 4,819,846 | Hannemann | Apr. 11, 1989 |
| 4,849,863 | Gallegos | July 18, 1989 |
| 5,027,442 | Taylor | July 02, 1991 |
| 5,040,524 | Votel et al | Aug. 20, 1991 |
| 5,081,719 | Donnelly | Jan. 21, 1992 |
| 5,148,549 | Sydor | Sep. 22, 1992 |
| 5,176,131 | Votel et al | Jan. 05, 1993 |

A more in-depth description of each of the more pertinent patents follows:

U.S. Pat. No. 5,176,141

This Patent is directed to a back support. The back support 10 includes a waistband 11 having a left half 12 and a right half 13, and suspenders 25 secured to the top edge 12 and 13 of a waistband 11. Fabric members 19 and 20 are stitched to the outside of the right half 13 and left half 12, respectively, and hook material 21 is secured to the inside of the left half 12 for securing the back support on the wearer. Referring to FIG. 3, a tool belt 50 is attached to the waistband 11. A variety of carriers or attachments, such as a strap 55 or a pouch 56 may be attached to the belt 50.

U.S. Pat. No. 3,963,157

This Patent is directed to a ball belt. The ball belt comprises a waistband 1 and a plurality of holders or pouches 2 detachably mounted on the waistband 1. Any style fastener may be attached to each end of the waistband 1. The pouch is slidably mounted on the waistband.

U.S. Pat. No. 2,976,541

This Patent is directed to a utility belt. The utility belt 10 comprises a flexible strap 12 having fastening means attached at each end, a receptacle 17 and 23 slidably mounted on the strap 12.

U.S. Pat. No. 4,819,846

This patent is directed to a sportsman's belt. Referring to FIG. 2, the belt 1 has straps 6 of pad material provided on its free ends for releasably securing the belt on a wearer, and a plurality of pouches 2 secured to the belt 1 by pad strips 9 affixed to the belt and to the pouches. It should be noted that both the belt 1 and pouches 2 are provided with second pads and strips 8 assembled to the pouch which can be folded over to close it.

U.S. Pat. No. 4,166,557

This Patent is directed to a belt attaching hanger. The hanger attachment 10 is slidably mounted on a conventional belt 11 and is provided with a wire support 20. As shown in FIG. 5, a tape row 25 is secured to the wire support 20.

U.S. Pat. No. 4,139,130

This Patent is directed to a canteen belt. The canteen belt 10 has an envelope shaped pocket 12 formed by the two sides for belt 11 and 13 enclosed by flap 17, hook 16 and pawl 18 fasteners at the ends of the belt for securing the belt on a wearer, and a pawl mounting pad 20 located on the outside of the belt, a water storage pouch 32 contained with pocket 12, a mouthpiece assembly 49 for the water storage pouch 32. Mouthpiece assembly 49 is attached to the pawl mounting pad 20 where the former is not in use.

SUMMARY AND OBJECTS OF THE INVENTION

It is an object of the invention to provide a unique tool belt construction for use individually or in conjunction with a back support.

It is another object of the invention to provide a uniquely constructed back support having an associated utility pouch belt support.

It is still another important object of the invention to provide a suspender supported back support having a tool belt component which is adapted to receive one or more slip-on pouches and to securely hold them in a fixed position relative to the waist of the wearer.

It is still another important object of the invention to provide a suspender supported tool belt and back support device which is easy to put on and take off.

It is still another important more specific object of the invention to provide a suspender supported tool belt and back support member which has a wide range of adjustability with respect to the wearer of the device.

It is still another important and even more specific object of the invention to provide a back support and utility pouch belt support member which is capable of providing loop and hook surfaces on a plurality of surfaces so that the back support and utility pouch belt may be secured in one or a plurality of positions and to accommodate the releasable securement of small tools to which have been placed mating hook and loop surfaces.

It is still another more important and specific object of the invention to provide a suspender supported, back support member which has releasably secured front suspender straps which have hook and loop fastener surfaces for full adjustability of sizes to accommodate a variety of body shapes.

It is still another and even more important and specific object of the invention to provide a back support and utility belt member wherein the waistband of the member is provided with loop and hook fastener surfaces for releasable engagement of the ends of the member so as to be fully adjustable over a wide range of waist sizes to accommodate a plurality of body shapes.

Generally the invention pertains to a utility belt by itself or in combination with a back support wherein the back support is for providing abdominal and lumbosacral support for the wearer. The improvement comprises a hook and loop fastener surface on a portion of the exterior surface of said back support and includes a belt member encircling at least a portion of said back support wherein the belt member has an interior and exterior surface, and a portion of at least the interior surface of the belt has a hook and loop fastener surface and wherein the belt configuration is adapted to receive one or more pouches or the like in one of a plurality of selected positions relative to the back support.

In its simplest form of a tool belt support member for utility pouches or containers, the invention comprises essentially first and second belts, both surfaces of the belts being provided with cooperating hook and loop fastener surfaces so that a pouch or the like may be slidably disposed on one belt and securely but releasably affixed to the juxtapositioned belt to adequately support the pouch or the like so that the same does not slide relative to the supporting belts.

These and other objects of the invention will become apparent from the hereinafter following commentary taken in conjunction with the drawings.

BRIEF DESCRIPTION OF THE DRAWINGS

FIG. 1 is a front view of one of the supports of the invention illustrating the same in relationship to a wearer who is shown in phantom line;

FIG. 2 is a view of one of the members of the invention showing more details of construction thereof;

DETAILED DESCRIPTION OF A PREFERRED EMBODIMENT

Figure 3:
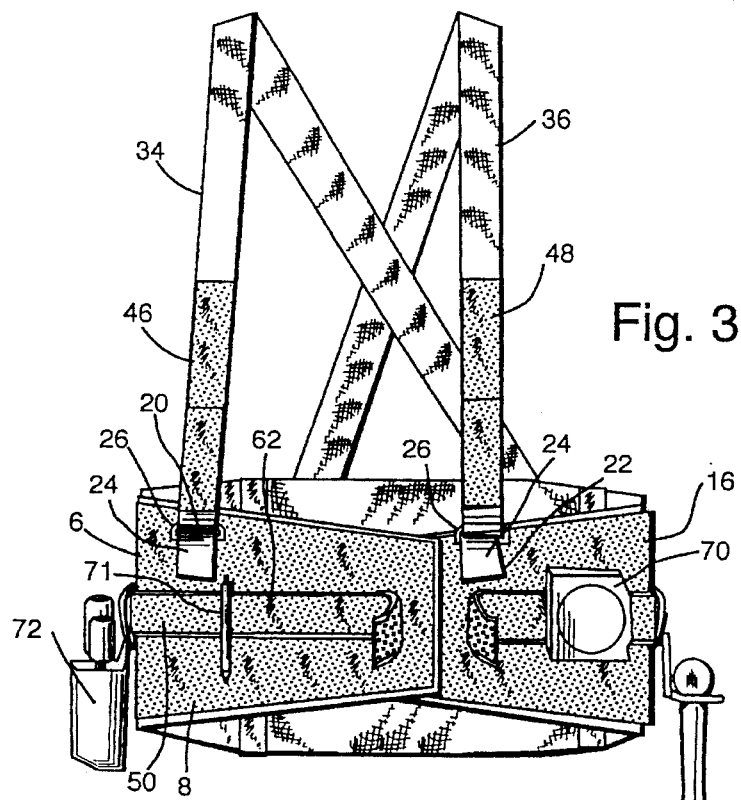
FIG. 3 is a front view of one of the support members of the invention depicted in FIGS. 1 and 2 showing more construction details thereof.

Referring to the drawings wherein like numerals of reference designate like elements throughout, it will be noted that the device of the invention 2 in this particular invention takes the form of a combination utility belt and back support wherein the device is comprised of a cumberbund-like, waist encircling portion 4 made up of a first panel 6 of relatively nonstretchable material, the exterior surface of which 8 is provided with a hook and loop fastener surface for purposes to be described. Connected to first panel 6, as by stitching or the like, is a first stretchable panel 9 with intermediate stiffening rib or slat 10 of thin unitary plastic or the like. Spaced about the midsection of portion 9 are second and third stiffening ribs or slats 12 of similar construction to stiffening rib or slat 10.

Attached to the end of stretchable segment 9 is an additional stiffening rib or slat 14 and each of the stiffening members 10, 12 and 14 are covered over with material and held in place by stitched seam lines, not shown, running the entire length of the stiffening members and being tightly secured to expansible segment 9.

Secured to the end of expansible segment 9 along the line determined by the stiffening member 14 by stitching or the like, is second panel 16 having a mirror image configuration of panel 6 and having its exterior surface 18 provided with hook and loop fastener surface material.

The panels 6 and 16 are made up of somewhat porous, breathable material which is relatively nonstretchable and is easily sewn in the fabrication process.

It will be noted that the panels 6 and 16 have somewhat of a taper portion on each of their termini to better accommodate the waist of a wearer, as shown in dotted line in FIG. 1.

To the front portions 6 and 16 at about the points 20 and 22, a singular tab 24 of nonstretchable material is sewn so as to create a loop in order to secure D-rings 26 in secured and retained relationship.

To the back surface of stretchable panel 9 are sewn rear loops 28 having reinforcement tabs 30 forming a loop in which to captively secure rear D-rings 32.

Suspender straps 34 and 36 are elongated slightly stretchable strips of material each of which has termini 38, 40, 42, and 44 provided with cooperatively mating hook and loop fastener surfaces for engagement through the D-rings 24 and 28 as seen in the drawings, such that the suspenders 34 and 36 are fully adjustable to accommodate the body size and configuration of the wearer of the device 2 of the invention. It should also be noted that the exterior surfaces at 46 and 48 of suspenders 34 and 36 are provided with one of a mating surface of hook and loop fastener so as to be able to have adhered to it, should it be desired, a tool such as a pencil or tape measure having adhered to it the opposite of the mating surface so that the tool may be readily and releasably secured to the suspender sections 46 and 48.

Stitchedly secured to the back elastic panel 9 in the area of the slats 12, is encircling elongate belt 50 which has an elastomeric portion 52 between the two vertical slats 12 which provide rigid support to elastomeric segment 9. The portion of belt 50 between the two juxtapositioned slats 12 is secured to the underlying panel 9 by means of stitching 54 extending the contiguous length of the width of the belt 50 at the supporting slats 12.

The interior surface 60 of belt 50 is provided with a mating hook and loop fastener surface so as to readily engage the adjacent hook and loop fastener surface of panels 6 and 16, more specifically the hook and loop fastener surfaces 8 and 18 respectively, provided on the exterior surfaces thereof.

Additionally, belt 50 is provided with an exterior surface 62 having a hook and loop fastener surface over a major portion thereof with exception of the elastomeric expansible section 52 in the rearward secured portion thereof as previously described, so as to be able to retain a tool such as a tape measure 70 or pencil 71 to a surface of which has been affixed a mating hook and loop fastener surface so as to be readily engageable to the exterior surface 62 of belt 50, as shown in FIG. 3.

By reason of the co-acting hook and loop fastener surfaces 8 and 18, and the interior cooperating and mating hook and loop fastener surface 60 of belt 50, a pouch or utility container such as 72, formed with the loop or flap 74 (or, alternatively, spaced slits), is easily received on the belt 50 and is securely and releasably held in a selected position by reason of the belt 50 inner hook and loop surface 60 engaging, in secure fashion, the juxtapositioned hook and loop fastener surface of surfaces 18 and 6 of segments 18 and 8, respectively. That is, a releasable connection and securement line is formed on either side of the loop 74 of pouch 72 so that the pouch 72 does not freely ride on the belt 50, but rather is rigidly and securely retained so as not to slip and cause displacement of the tools and the like contained within the pouch 72, and the pouch 72 itself.

It is obvious that additional pouches may be supported on both sides of the inventive device 2, depending upon the needs of the workman or other person utilizing the member 2 of the invention. A single front supported pouch may also suffice for some conditions.

Figure 4:
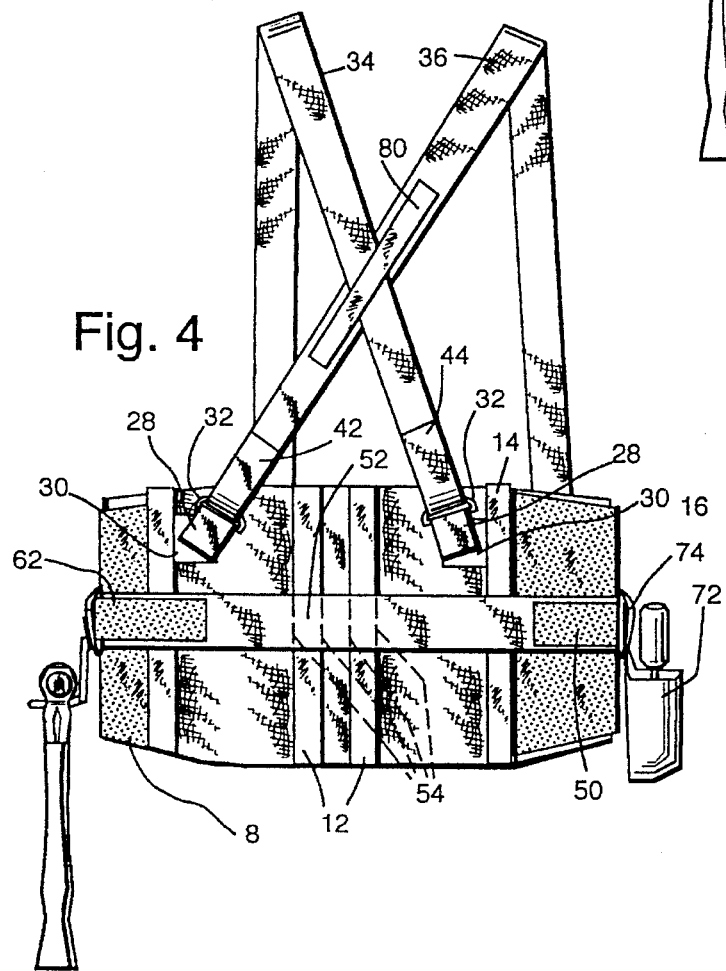
FIG. 4 is a rear view of the member shown in FIG. 3.

Referring to FIG. 4, it will be noted that a loop member 80 comprising a strip of material sewn at the terminal ends onto the back surface of suspender 36 is provided so as to provide a guide or confining means for suspender 34 which prevents the suspenders 34 and 36 from becoming dislodged and misaligned with respect to the back of the wearer.

The fabric of construction for each of the components making up the support member 2 of the invention are as follows:

Suitable Materials of Construction

1. Segments 6 and 16 may consist of loop to foam to nylon laminate
2. Elastic panel 9 may consist of medical knit elastic
3. Belt material 50 may be medical truss elastic and back-to-back hook to loop laminate
4. Suspender material 34–36 may be medical truss elastic
5. Hook and loop surface material may be nylon
6. Plastic D-ring material may be of "DELRIN"
7. Thread used to sew may be of nylon Those of ordinary skill in the art will be knowledgeable of other materials of construction and of the relative size, thickness and elasticity, where needed, in order to practice the herein described invention.

With the herein disclosed inventive support, it will be noted that the device 2 may be used by a carpenter or other tradesman or the like for carrying tools and it should be understood by reason of the hook and loop suspender attachments, that in removing the supported device as shown in FIG. 1, one merely opens up the belt 50 from its retained hook and loop fastening position, and opens up and separates the panel 6 from 16 which is also held in hook and loop fashion, as shown in FIG. 2 and then releasing the one strap such as 34 from its relationship if desired to be able to remove the device 2 from the wearer in a facile manner. If desired, depending upon the user's body configuration, the user may trim excess length off of the belt 50 so that the same does not overlap onto the contiguous portion of the device 2 to too great an extent, thereby allowing the use of one hand to disassociate the belt 50 from engagement.

It should be understood that while the device 2 has been illustrated with respect to tradesmen's tools and the like, the pouches 72 may be modified in size and configuration to accept other loads such as rivets, coins, or any such material where the wearer of the device 2 is expected to spend long hours on his or her feet with a substantial load contained within the utilitarian pouch or pouches.

Those of ordinary skill in the art will at once recognize that various changes and modifications in both specific configuration and materials of construction can be made with respect to the disclosed invention and all such changes and modifications are intended to be covered by the appended claims.

For example, one change and modification could be the elimination of suspenders if the wearer of the device 2 is not concerned about off-bearing some of the carried load onto the shoulders. In this event, it is easy to modify the device 2 by eliminating not only the suspenders, but also the supporting D-rings and material attachments.

Furthermore, where the wearer of the device 2 is not interested so much in back support but merely in being able to have a belt construction for receiving conventional pouches, having slide loops and the like in secure fashion, the panels 6, 9 and 16 may be made much narrower, just slightly larger than the belt 50 so as to obtain the attributes of having a device 2 that supports utility pouches in quick, easily releasable and secure fashion.

These and other modifications and changes will make themselves apparent to those of ordinary skill in the art.

We claim:

1. In a utility belt and back support for providing abdominal and lumbosacral support for the wearer, the improvement comprising:

a first broad longitudinally extended belt member having a width sufficiently broad to engage a substantial portion of the lumbar region of a wearer's back to provide support thereto and having a stretchable rear portion, said rear portion having a plurality of transversely directed rib members secured thereto for aiding in the support of a user's back, said first belt member having a pair of tapered portions on opposing ends thereof, said first belt member having opposing interior and exterior surfaces;

a hook and loop fastener surface disposed on said exterior surface of said pair of tapered portions of said first belt member, said interior surface of one of said pair of tapered portions of said first belt member having a hook and loop fastener secured thereto for releasable coupling with said hook and loop fastener surface of said first belt member exterior surface subsequent to said first belt member being wrapped around a user's waist;

a second belt member encircling said first belt member, said second belt member being narrower than said first belt member, said second belt member having an interior and exterior surface, a portion of at least the interior surface of said second belt having a hook and loop fastener surface for releasable engagement with said hook and loop fastener surface of said first belt member, said second belt member having a configuration adapted to receive and retain holding means for holding articles in one of a plurality of selected positions relative to said first belt member; and holding means for holding articles, said holding means adapted for reception by said second belt member.

2. The improvement in accordance with claim 1 wherein said holding means has an enclosed upper portion through which said belt passes.

3. The improvements in accordance with claim 1 wherein said holding means for holding articles is provided with attachment means for attachment through which said belt is threaded.

4. The improvement in accordance with claim 1 wherein said second belt member is fixedly secured to said first belt member.

5. The improvement in accordance with claim 4 wherein said first belt member has suspenders affixed thereto adapted to engage the shoulders of the wearer of said first belt member.

6. The improvement in accordance with claim 5 wherein said suspenders are pivotably secured to said first belt member.

7. The improvement in accordance with claim 6 wherein said suspenders are affixed to said first belt member using D-rings.

8. The improvement in accordance with claim 6 wherein said suspenders are secured to said first belt member in criss-cross fashion.

9. The improvement in accordance with claim 8 wherein one suspender adapted for positioning on the back of the wearer has a loop through which the other back suspender passes.

10. The improvement in accordance with claim 9 wherein the front portion of each of said suspenders is releasably secured to said first belt member.

11. The improvement in accordance with claim 10 wherein said suspenders are releasably secured through hook and loop surfaces interaction.

12. The improvement in accordance with claim 11 wherein the exterior from surfaces of said suspenders and the majority of the front surface of said first belt member are provided with hook and loop surfaces for receiving and releasably retaining tools and the like having a mating hook and loop surface affixed thereto.

13. The improvement in accordance with claim 12 wherein said second belt member is adapted to receive and retain in releasable engagement two pouches in spaced relationship on either side of the wearer of said first belt member.

14. A back support for providing abdominal and lower back support for the wearer comprising the combination:

(a) a waistband having a width sufficiently broad to engage a substantial portion of the lumbar region of a wearer's back to provide support thereto adapted to encircle the waist of the wearer and having opposed end sections adapted for engagement to each other, said opposed end sections being formed by a hook and loop fastener surface, said waistband having a stretchable section located intermediate said opposed end sections and disposed contiguous with the wearer's back, said stretchable section having at least one substantially vertically directed rib member secured thereto;

(b) a belt coupled to said waistband and having an inner surface at least a portion of which has a hook and loop surface adapted to be releasably engaged to said hook and loop surface of said end sections of said waistband and being adapted to encircle the waist of the wearer and being adapted to receive a holding means for holding articles in selected positions relative to said belt; and (c) holding means for holding articles, said holding means adapted for reception by said belt.

15. The back support in accordance with claim 14 which additionally includes means for suspending said back support from the shoulders of the wearer.

16. The back support in accordance with claim 15 wherein said holding means is slidably positionable and said belt may be selectively secured to said back support adjacent either side of said holding means whereby said holding means is fixedly retained in non-slidable relationship to said back support.

17. The back support in accordance with claim 16 wherein said means for suspending said back support from the shoulders of the wearer comprise criss-cross suspenders, the fronts of which are releasably and operatively affixed to the front of said back support.

18. The back support in accordance with claim 17 wherein the rear termini of said suspenders are affixed to the back side of said back support through D-rings.

19. The back support in accordance with claim 18 wherein a majority of the front surface of said waistband has a hook and loop surface, and a front portion of each of said suspenders is provided with a hook and loop surface.

20. A utility belt comprising the combination of:

an elongated first belt having a width sufficiently broad to engage a substantial portion of the lumbar region of a wearer's back to provide support thereto having interior and exterior surfaces and opposing first and second ends, said first belt being adapted to encircle a user's waist and having a stretchable portion located intermediate said first and second ends and disposed contiguous with the user's back, said stretchable portion having at least one rib member secured transversely thereacross, said interior and exterior surfaces each having a portion thereof with respective hook and loop fastening surfaces adjacent said first and second ends for releasable engagement with each other;

a second belt adapted to encircle said first belt and being adapted to receive means for holding articles in slidable fashion therewith, said second belt having a hook and loop fastening surface on an interior surface thereof:

holding means for holding articles, said holding means adapted for reception by said second belt;

said second belt being adapted to be secured to said first belt at least in areas contiguous to said holding means, whereby said holding means is securely retained relative to said first and second belt.

* * * * *